(12) United States Patent
Fujimura et al.

(10) Patent No.: US 8,088,570 B2
(45) Date of Patent: Jan. 3, 2012

(54) METHOD FOR SCREENING AN AGENT FOR PREVENTING OR AMELIORATING WRINKLES

(75) Inventors: Tsutomu Fujimura, Ichikai-machi (JP); Takuji Kume, Tokyo (JP); Akira Hachiya, Cincinnati, OH (US)

(73) Assignee: Kao Corporation, Tokyo (JP)

( * ) Notice: Subject to any disclaimer, the term of this patent is extended or adjusted under 35 U.S.C. 154(b) by 613 days.

(21) Appl. No.: 11/405,471

(22) Filed: Apr. 18, 2006

(65) Prior Publication Data

US 2007/0243520 A1     Oct. 18, 2007

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS

| | | | | |
|---|---|---|---|---|
| 5,994,081 | A | * | 11/1999 | Tang et al. .......................... 435/6 |
| 6,221,911 | B1 | * | 4/2001 | Lavin et al. ..................... 514/567 |
| 2003/0119715 | A1 | * | 6/2003 | Ward et al. ......................... 514/1 |

OTHER PUBLICATIONS

Blumenberg, Intermediate Filaments. 2006. Transcriptional Regulation of Keratin Gene Expression. p. 100.*
Tomic-Canic et al. Experimental Cell Research 224, 96-102. 1996, p. 97.*
Kinouchi et al. (Arch Dermatol Res. 2002. 293: 634-641).*
Gazel et al. (J Invest Dermatol, 2003. 121:1459-1468).*
Bernerd et al. (J Invest Dermatol, 2001. 117:1421-1429).*
Smith et al. (J Invest Dermatol, 1994. 102:433-439).*
West et al. (J. Invest Dermatol, 1992; 99:95-100).*
Del Bino et al. (British Journal of Dermatology 2004; 150: 658-667).*
Sano et al. (Arch Dermatol Res. 296: 359-365, published online Dec. 14, 2004).*
Del Bino et al, British Journal of Dermatology 2004: vol. 150, pp. 658-667.
Bayerl et al, Photodermatol Photoimmunol Photomed., 1995, vol. 11, pp. 149-154.
Yamada et al, Molecular Biology of the Cell, 2002, vol. 13, pp. 382-391.
Sano et al, Arch Dermatol Res., 2005, vol. 296, pp. 359-365.
Paladini et al, Journal of Cell Biology, 1996, vol. 132, No. 3, pp. 381-397.
Yamada et al, Journal of Structural Biology, 2003, vol. 143, 45-55.
U.S. Appl. No. 12/772,334, filed May 3, 2010, Fujimura.

* cited by examiner

*Primary Examiner* — Scott Long
(74) *Attorney, Agent, or Firm* — Oblon, Spivak, McClelland, Maier & Neustadt, L.L.P.

(57) ABSTRACT

There is provided a screening method which can select a photoaging-preventing or improving agent or a wrinkle-preventing or improving agent with efficiency and reliability. The screening method for a photoaging- or wrinkle-preventing or improving agent selects, as a candidate, a substance inhibiting the expression of keratin 6 and/or keratin 16 genes or keratin 6 and/or keratin 16 proteins in a skin tissue or cell.

18 Claims, 5 Drawing Sheets

Fig. 1

**P<0.01, Kruskal-Wallis Test

METHOD FOR SCREENING AN AGENT FOR PREVENTING OR AMELIORATING WRINKLES

BACKGROUND OF THE INVENTION

1. Field of the Invention

The present invention relates to a screening method for a photoaging- or wrinkle-preventing or improving agent.

2. Background of the Invention

Cell aging, particularly skin aging, involves changes in appearance such as the formation of wrinkles and sags and reduction in skin elasticity. Therefore, there is a strong demand for the elucidation of an aging mechanism and for anti-aging remedy.

Heretofore, the formation of wrinkles and the like has been believed to have a strong relationship with ultraviolet rays, and skin aging caused by ultraviolet irradiation is called photoaging and has been studied in various ways. The present inventors have also reported that the elasticity of the stratum corneum, that is, epidermal elasticity, of hairless mice that have developed wrinkles due to chronic ultraviolet irradiation is significantly lower than that of unirradiated mice, indicating the relationship between wrinkles and epidermal elasticity, and that reduced keratin filament distribution (aggregation) attributed to the chronic ultraviolet irradiation was found to cause this reduction in the elasticity, resulting in the formation of wrinkles (Sano T, Kume T, Fujimura T, Kawada H, Moriwaki S, Takema Y: The formation of wrinkles caused by transition of keratin intermediate filaments after repetitive UVB exposure. Arch. Dermatol. Res. 2005; 296: 359-365).

On the other hand, the properties and functions of epidermal tissues are mostly determined and maintained by cornification, that is, the differentiation program unique to epidermal keratinocytes. The skeletal structure of the cornified cell is mechanically maintained by keratin proteins. Approximately 20 or more kinds of keratin proteins have been found out so far, of which keratin 5 (K5), keratin 14 (K14), keratin 1 (K1), and keratin 10 (K10) proteins are known to be expressed in facial skins and so on while hyperproliferative keratin proteins such as keratin 6 (K6) and keratin 16 (K16) proteins are known to be expressed in wounded or overstimulated tissues. The composition of these keratin proteins has been shown to control the mechanical properties of keratin filaments (Yamada S, Wirtz D, Coulombe P A: Pairwise assembly determines the intrinsic potential for self-organization and mechanical properties of keratin filaments. Mol. Biol. Cell. 2002; 13: 382-391; Yamada S, Wirtz D, Coulombe P A: The mechanical properties of simple epithelial keratins 8 and 18: discriminating between interfacial and bulk elasticities. J. Struct. Biol. 2003; 143: 45-55; and Paladini R D, Takahashi K, Bravo N S, Coulombe P A: Onset of re-epithelialization after skin injury correlates with a reorganization of keratin filaments in wound edge keratinocytes: defining a potential role for keratin 16. J. Cell Biol. 1996; 132: 381-397).

However, the detailed relationship between skin photoaging or wrinkle formation and keratin proteins has not been elucidated.

SUMMARY OF THE INVENTION

The present invention relates to the following inventions:

1) a screening method for a photoaging- or wrinkle-preventing or improving agent, which selects, as a candidate, a substance inhibiting the expression of keratin 6 and/or keratin 16 genes or keratin 6 and/or keratin 16 proteins in a skin tissue or cell;

2) a screening method for a photoaging- or wrinkle-preventing or improving agent, including the following steps (1) to (4):

(1) bringing a test substance into contact with a skin tissue or cell having the enhanced expression of keratin 6 and/or keratin 16 proteins;

(2) extracting epidermal keratin proteins from the skin tissue or cell;

(3) measuring expression levels of keratin 6 and/or keratin 16 proteins in the extracted epidermal keratin proteins to compare the expression levels with those in a control skin tissue or cell not brought into contact with the test substance; and (4) selecting the test substance decreasing the expression levels of keratin 6 and/or keratin 16 proteins as a photoaging- or wrinkle-preventing or improving agent, based on the result of the step (3); and 3) a screening method for a photoaging- or wrinkle-preventing or improving agent, comprising the following steps (1) to (3):

(1) bringing a test substance into contact with a skin tissue or cell having the enhanced expression of keratin 6 and/or keratin 16 genes;

(2) measuring expression levels of keratin 6 and/or keratin 16 genes in the tissue or cell brought into contact with the test substance to compare the expression levels with those in a control skin tissue or cell not brought into contact with the test substance; and (3) selecting the test substance decreasing the expression levels of keratin 6 and/or keratin 16 genes as a photoaging- or wrinkle-preventing or improving agent, based on the result of the step (2).

DETAILED DESCRIPTION OF THE PREFERRED EMBODIMENTS

The present invention is intended to provide a screening method which can select a photoaging- or wrinkle-preventing or improving agent with reliability and efficiency.

The present inventors have biochemically studied a mechanism of epidermal elasticity reduction in chronically ultraviolet-irradiated hairless mice. Consequently, the present inventors have found that of epidermal keratin proteins, keratin 6 (K6) and keratin 16 (K16) proteins and their genes exhibit expression remarkably increased in skin tissues that have developed wrinkles, and that the use of expression levels of the proteins or the genes as an index allows for the screening of a photoaging- or wrinkle-preventing or improving agent.

According to the present invention, a photoaging- or wrinkle-preventing or improving agent can be selected with reliability and efficiently.

Hereinafter, the screening method of the present invention will be described.

The screening method for a photoaging- or wrinkle-preventing or improving agent of the present invention selects, as a candidate, a substance inhibiting the expression of K6 and/or K16 genes or K6 and/or K16 proteins in a skin tissue or cell.

The substance inhibiting the expression of K6 and/or K16 proteins refers to a substance that suppresses the expression of K6 and/or K16 proteins and decreases expression levels thereof. The substance inhibiting the expression of K6 and/or K16 genes refers to a substance that suppresses the expression of mRNAs encoding K6 and/or K16 proteins.

In this context, the K6 protein is one of neutral-basic type II keratin proteins, and the K16 protein is one of small, acidic type I keratin proteins. Heterodimers formed by type I and type II keratins are essential to keratin filament formation, and the K6 and K16 proteins in a pair form a heterodimer. Moreover, both the proteins have been reported to be hyperproliferative keratin proteins and to be expressed in wounded or overstimulated tissues (J. Cell Biol. 1996; 132: 381-397).

Figure 2:
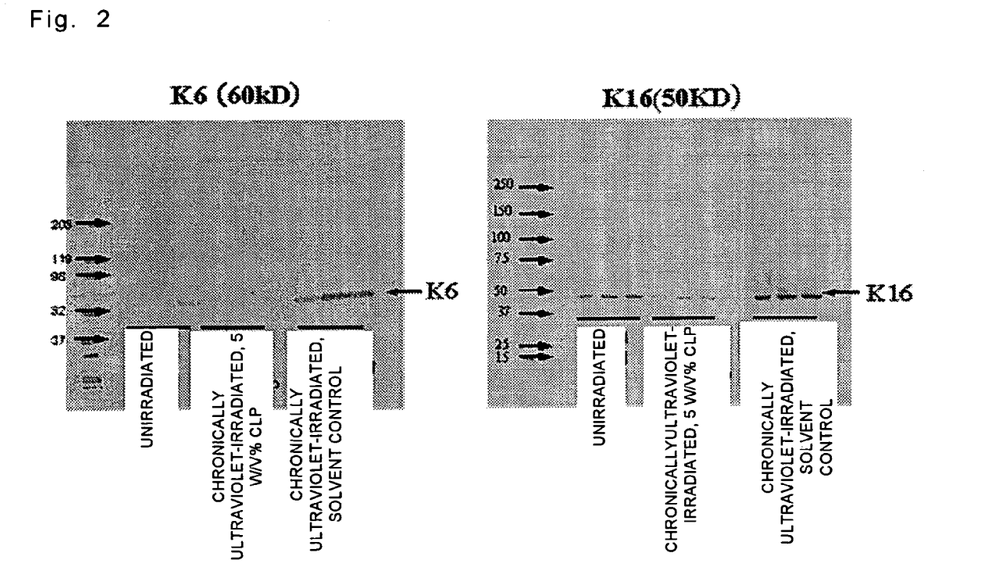
FIG. 2 is a diagram showing western blotting results of K6 and K16 proteins.
Figure 3:
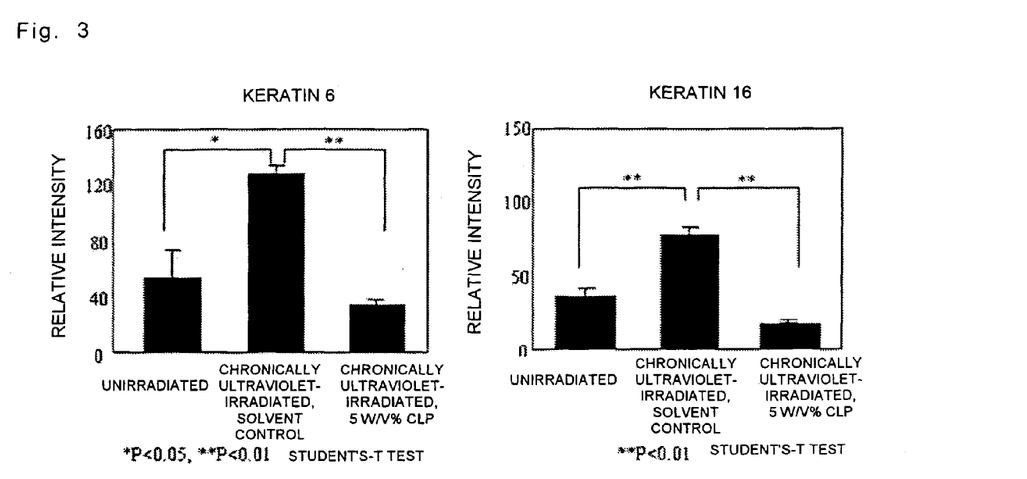
FIG. 3 is a diagram showing quantification results of K6 and K16 proteins.
Figure 4:
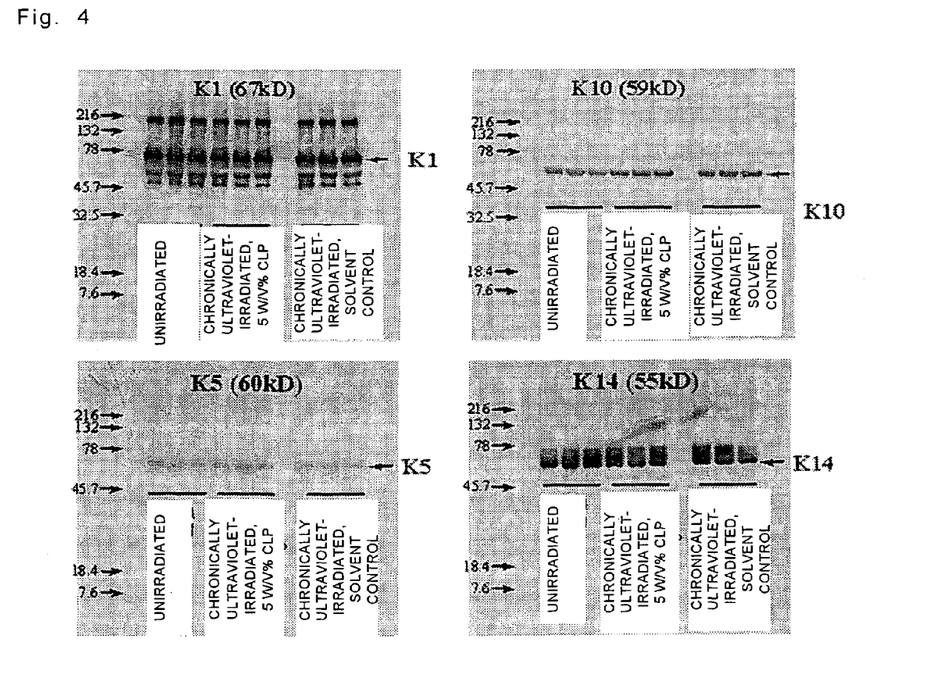
FIG. 4 is a diagram showing western blotting results of K1, K10, K5, and K14 proteins.
Figure 5:
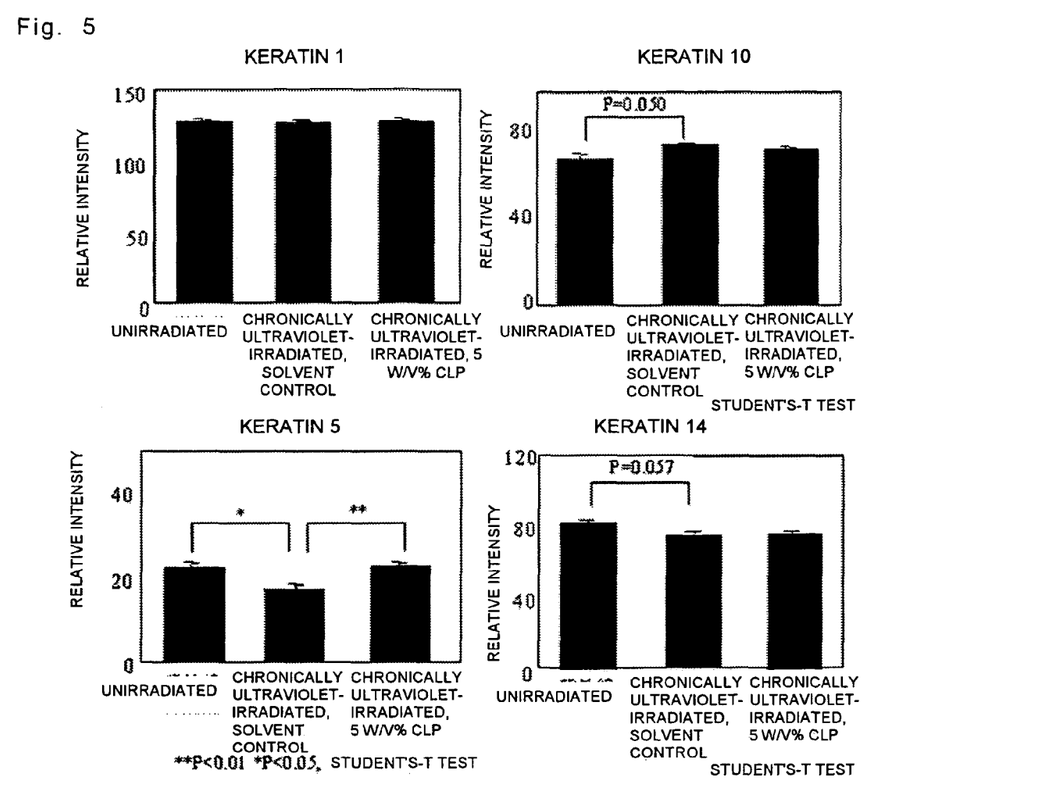
FIG. 5 is a diagram showing quantification results of K1, K10, K5, and K14 proteins.

In the analysis of changes (keratin types and protein expression levels) in keratin proteins in the epidermis that had developed wrinkles due to chronic ultraviolet irradiation, protein levels of keratin 1 (K1), keratin 10 (K10), keratin 5 (K5), and keratin 14 (K14) proteins were hardly changed whereas protein levels of K6 and K16 proteins were remarkably increased, as shown in Example 1 below. When carbamimidoyl-L-proline (CLP) (Reference Example 1 and U.S. Pat. Nos. 6,436,920 and 6,306,848) known to have the effect of recovering the elasticity of the stratum corneum and to be effective in the prevention and improvement of wrinkles was applied thereto, the protein levels of the K6 and K16 proteins increased due to the chronic ultraviolet irradiation were decreased to unirradiated levels (FIGS. 2 and 3). On the other hand, the protein levels of the K1, K10, K5, and K14 proteins were hardly changed by the CLP application (FIGS. 4 and 5).

In the analysis of inhibitory effects on wrinkle formation caused by chronic ultraviolet irradiation and of changes (keratin types and protein expression levels) in epidermal keratin proteins, protein levels of K6 and K16 proteins were decreased (FIG. 7, upper) by the application of carbamimidoyl-L-proline (CLP) (Reference Example 1 and U.S. Pat. Nos. 6,436,920 and 6,306,848) whereas protein levels of K1, K10, K5, and K14 proteins were hardly changed (FIG. 7 middle and lower) by the CLP application, as shown in Example 2 below.

These results suggest that the expression of K6 and K16 proteins are deeply involved in wrinkle formation, and that a substance inhibiting their expression is useful as a photoaging- or wrinkle-preventing or improving agent that inhibits wrinkle formation in skins or improves formed wrinkles, and a photoaging- or wrinkle-preventing or improving agent can be screened with expression levels of K6 and/or K16 proteins as an index.

In the analysis of changes (keratin types and gene expression levels) in expression levels of keratin genes in wrinkle model skin tissues constructed by chronic ultraviolet irradiation on human skin grafts transplanted to the skins of immunodeficient animals, expression levels of K1, K5, and K10 genes were hardly changed whereas expression levels of K6 and K16 genes were remarkably increased, as shown in Example 3 below.

The skin tissue or cell used in the present invention may be a skin tissue or cell derived from a non-human animal having the excessive expression of K6 and/or K16 genes or K6 and/or K16 proteins, and preferably, has expression levels of the genes or the proteins increased by approximately 120% to 500% compared with those in a normal skin tissue or cell. Examples of the animal from which the skin tissue or cell is derived include rodents such as mice, rats, and guinea pigs.

Preferable examples of such a skin tissue or cell include wrinkled skin tissues of wrinkle model animals constructed by chronic ultraviolet irradiation, and cells present in the tissues (1) Tramposch K M, Nair X, Gendimenico G J, Tetrault G B, Chen S, Kiss I Whiting G, Bonney R J: The pharmacology of a novel topical retinoid, BMY 30123: comparison with tretinoin. J. Pharm. Pharmacol. 1992; 44: 379-386; and 2) Kiss I, Chen S, Tramposch KM: The effect of high and low ultraviolet-B dose exposure on the degree of hairless mouse skin wrinkling. Photochem. Photobiol., 1991; 53: 109-112).

It is particularly preferred to use the skins of model animals constructed by the following procedures (see Reference Example 1): 6- to 10-week-old hairless mice are exposed once a day and three to seven times a week for 6 to 20 consecutive weeks to ultraviolet rays of 1 MED (minimum erythema dose) or lower, that is, at a dose of 141 to 470 J/m$^2$ during the 0th (at the start of irradiation) to first weeks, at a dose of 159 to 530 J/m$^2$ during the first to second week, at a dose of 198 to 600 J/m$^2$ during the second to third week, and at a dose of 201 to 670 J/m$^2$ during the fourth and subsequent weeks.

The skin tissue or cell used in the present invention can be derived from a human. Preferable examples of such a skin tissue or cell include wrinkled skin tissues of wrinkle model skins constructed by chronic ultraviolet irradiation on human skin grafts transplanted to the skins of immunodeficient non-human animals, preferably immunodeficient mice (e.g., SCID mice and Nude mice), and cells present in the tissues (U.S. patent application Ser. No. 11/311,239). It is particularly preferred to use a skin tissue or cell obtained from the human skin grafts transplanted to the skins of immunodeficient non-human animals, preferably immunodeficient mice, exposed to ultraviolet-B rays at a dose of 80 to 100 mJ/cm$^2$ for 4 to 8 consecutive weeks and left for at least 3 weeks after irradiation, more preferably exposed to the ultraviolet-B rays for 6 to 8 consecutive weeks and left for 1 day to 8 weeks after irradiation.

In the screening method of the present invention, the selection of a candidate substance with expression levels of K6 and/or K16 proteins as an index is specifically performed by the following steps:

(1) bringing a test substance into contact with a skin tissue or cell having the enhanced expression of K6 and/or K16 proteins;

(2) extracting epidermal keratin proteins from the skin tissue or cell;

(3) measuring expression levels of K6 and/or K16 proteins in the extracted epidermal keratin proteins to compare the expression levels with those in a control skin tissue or cell not brought into contact with the test substance; and (4) selecting the test substance decreasing the expression levels of K6 and/or K16 proteins as a photoaging- or wrinkle-preventing or improving agent, based on the result of the step (3).

The contact of the test substance into the skin tissue in the step (1) can be performed by applying a solution of the target substance (0.01 to 30 w/v %) dissolved in a solvent such as ethanol and water to the dorsal skins of mice or to human skin grafts transplanted to immunodeficient non-human animals, preferably immunodeficient mice for a given period, for example applying 100 μL/application of the solution to the dorsal skin of one wrinkle model mouse once a day and five times a week or applying 50 μL/application of the solution to the human skin graft transplanted to the skin of the immunodeficient non-human animal once a day and five times a week.

The extraction of the epidermal keratin proteins in the step (2) can be performed by adopting, for example, a method by which after the skins collected from the animals are cooled on ice immediately after treatment in distilled water at 60° C. for 1 minute or treated with dispase at 37° C. for 5 to 60 minutes, epidermal portions are separated from the dermis with a spatula, followed by the homogenization of the obtained epidermal portions (containing the stratum corneum) in a urea buffer.

The expression levels of K6 and/or K16 proteins can be quantified by a method known in the art such as western blotting using, for example, keratin antibodies recognizing K6 or K16 proteins such as anti-mouse keratin 6 antibodies (Covance, Berkeley Antibody Company), anti-cytokeratin 6 antibodies (Gene Tex, Inc.), anti-human keratin 6 antibodies (Lab Vision), anti-human keratin 16 antibodies (Lab Vision), and anti-human keratin 16 antibodies (Spring Bioscience).

The western blotting can be enforced by using the antibody of the present invention as a primary antibody, then using an antibody binding to the primary antibody and labeled with a radioisotope (e.g., 125I), fluorescent material, or enzyme (e.g., horseradish peroxidase (HRP)) as a secondary antibody to perform labeling, and measuring signals derived from these labeling substances with a radiation counter, fluorescence detector, or the like.

The antibody may be a polyclonal antibody using the K6 and/or K16 proteins as immunizing antigens or a monoclonal antibody thereof.

In the screening method of the present invention, the selection of a candidate substance with expression levels of K6 and/or K16 genes as an index is specifically performed by the following steps:

(1) bringing a test substance into contact with a skin tissue or cell having the enhanced expression of K6 and/or K16 genes;

(2) measuring expression levels of K6 and/or K16 genes in the tissue or cell brought into contact with the test substance to compare the expression levels with those in a control skin tissue or cell not brought into contact with the test substance; and (3) selecting the test substance decreasing the expression levels of K6 and/or K16 genes as a photoaging- or wrinkle-preventing or improving agent, based on the result of the step (2).

The contact of the test substance into the skin tissue or cell in the step (1) can be performed by applying a solution of the target substance (0.01 to 30 w/v %) dissolved in a solvent such as ethanol and water to the dorsal skins of mice or to human skin grafts transplanted to immunodeficient non-human animals, preferably immunodeficient mice for a given period, for example applying 100 μL/application of the solution to the dorsal skin of one wrinkle model mouse once a day and five times a week or applying 50 μL/application of the solution to the human skin graft transplanted to the skin of the immunodeficient non-human animal once a day and five times a week.

The detection and quantification of gene expression can be enforced by a method known in the art such as RT-PCR using RNA prepared from the tissue or complementary polynucleotide transcribed therefrom.

Based on the expression levels of K6 and/or K16 genes or K6 and/or K16 proteins thus quantified, a substance inhibiting the expression of the genes or the proteins can be selected. In this case, when the expression levels are statistically significantly low as compared with those in the control skin tissue, this test substance can be selected as the substance inhibiting the expression.

EXAMPLES

Reference Example 1

Wrinkle-Improving Effect of CLP

An experimental system of the chronic and continuous exposure of hairless mice to ultraviolet rays of minimum erythema dose (hereinafter, referred to as 1 MED) or lower (J. Pharm. Pharmacol. 1992; 44: 379-386; and Photochem. Photobiol., 1991; 53: 109-112) was used as a wrinkle formation model to perform a test of wrinkle improvement of 1-carbamimidoyl-L-proline (CLP) in vivo.

The mice used were hairless mice (Hr-1-ICR) produced from crossing between Hr-1 (Skh-1) hairless mice and ICR mice. Toshiba SE20 lamps were used as an ultraviolet source, and ultraviolet doses used were measured with UV-RADI-OMETER (UVR-305/365D, Eisai). The 6- to 10-week-old hairless mice were exposed once a day and five times a week for 12 consecutive weeks to ultraviolet rays of 1 MED or lower, that is, at a dose of 470 J/m$^2$ during the 0th (at the start of irradiation) to first week, at a dose of 530 J/m$^2$ during the first to second week, at a dose of 600 J/m$^2$ during the second to third week, and at a dose of 670 J/m$^2$ during the fourth and subsequent weeks, to prepare chronically ultraviolet-irradiated mice. Subsequently, 100 μL of 5 w/v % CLP solution (30 vol % ethanol solution) was applied once a week and five times a week for 6 consecutive weeks to the whole dorsal skin of each of the mice. For controls, 30 vol % ethanol solution was used. Each of the 5 w/v % CLP group and the control group comprised 14 mice.

Visual Observation Score

The degree of wrinkles formed on the dorsal skins of the mice was determined at the start of CLP application and on the 6th week according to a visual observation score with reference to the documents described above. The score was evaluated on a scale of 7 using the scores below and mean values.

Figure 1:
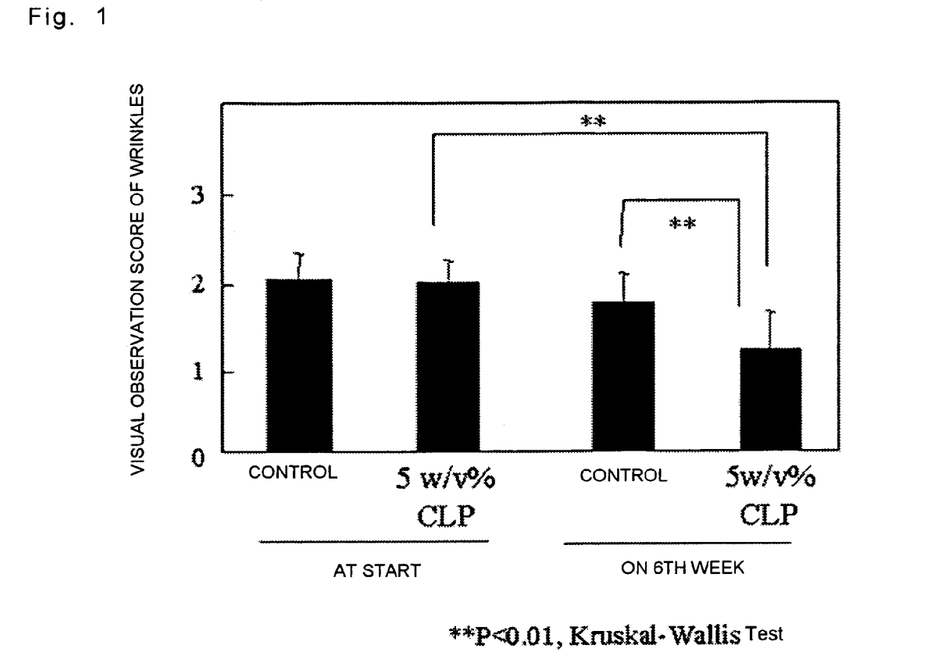
FIG. 1 is a diagram showing the wrinkle-improving effect of CLP (evaluation of visual observation score of wrinkles)

Score 0: no wrinkle observed
Score 1: wrinkles slightly observed
Score 2: wrinkles observed
Score 3: wrinkles remarkably observed As a result, no difference was observed between the control group and the 5 w/v % CLP group at the start. The visual observation score of the 5 w/v % CLP group was significantly decreased on the 6th week as compared with at the start and was significantly lower than that of the control group in terms of comparison on the 6th week. The wrinkle-improving effect of CLP was demonstrated (FIG. 1).

Example 1

Test of Inhibition of Epidermal K6 and K16 Protein Production in Hairless Mice

Six-week-old hairless mice of the same species as in Reference Example 1 were exposed for 9 consecutive weeks to ultraviolet rays at a dose of 470 J/m² during the 0th (at the start of irradiation) to first week, at a dose of 530 J/m² during the first to second week, at a dose of 600 J/m² during the second to third week, and at a dose of 670 J/m² during the fourth and subsequent weeks, to prepare chronically ultraviolet-irradiated mice (wrinkle model mice). Then, 100 μL of 5 w/v % CLP solution (50 vol % ethanol solution) was applied once a week and five times a week for 6 consecutive weeks to the whole dorsal skin of each of the mice to examine changes in epidermal keratin protein levels. For controls, 50 vol % ethanol solution (solvent control) and unirradiated age-matched mice (unirradiated mice) were used. Each of the groups comprised 3 mice.

Quantification of Keratin Proteins by Western Blotting

After the dorsal skins collected from the mice were cooled on ice immediately after treatment in distilled water at 60° C. for 1 minute, epidermal portions were separated from the dermis with a spatula. The obtained epidermal portions (containing the stratum corneum) were homogenized in a urea buffer (8 M urea, 50 mM tris-HCl (pH 7.6), 100 mM mercaptoethanol, 1 mM dithiothreitol, and protease inhibitors) to extract proteins. Insoluble matter was removed by centrifugation and supernatant collection. Following the measurement of the total protein concentration (RD DC Protein Assay Kit, Bio-Rad Laboratories Inc.), samples were prepared at the same concentrations. The samples were supplemented with laemmli buffer and treated at 90 to 100° C. for 3 to 5 minutes to give samples for electrophoresis. The samples were electrophoresed on 5 to 15% gradient acrylamide gel or 12.5% acrylamide gel (Bio Rad) at 60 V for 3 hours and blotted onto a nitrocellulose membrane at 250 mA for 1 hour under ice cooling. Following blocking with 2% skim milk, each type of mouse keratin (MK1, MK10, MK5, MK14, MK6, and MK16) antibody was allowed to act thereon at the optimum concentration. The MK1, MK10, MK5, MK14, and MK6 antibodies were rabbit polyclonal antibodies against MK1, MK10, MK5, MK14, and MK6 available from Covance, Berkeley Antibody Company, and the MK16 antibody was an antibody produced from an animal (rabbit) immunized with synthetic peptide as an antigen represented by $HN_2$-C-S-T-S-F-S-Q-S-Q-S-Q-S-S-R-D-COOH according to the document (Bernot K M, Coulombe P A, McGowan K M. Keratin 16 expression defines a subset of epithelial cells during skin morphogenesis and the hair cycle. J Invest Dermatol. 2002; 119(5): 1137-49). Labeling was performed by using peroxidase-labeled secondary antibodies, and color was developed by chemiluminescence method (ECL-Plus, Amersham Pharmacia Biotech) and detected with X-ray films. Quantification was performed with Adobe Photoshop (Adobe Systems Incorporated).

Western blotting results and quantification results of K6 and K16 protein levels are shown in FIGS. 2 and 3, respectively (mean+/−SD). The epidermal K6 and K16 protein levels in the chronically ultraviolet-irradiated mice were increased even after 6 weeks from the termination of ultraviolet irradiation, as compared with those in the unirradiated mice. On the other hand, the K6 and K16 protein levels increased due to the chronic ultraviolet irradiation was decreased to unirradiated levels by the CLP application. Alternatively, western blotting results and quantification results of K1, K10, K5, and K14 protein levels are shown in FIGS. 4 and 5, respectively (mean+/−SD).

No significant difference was observed among the K1, K10, and K14 protein levels by the chronic ultraviolet irradiation and by the 5 w/v % CLP application. Although significant difference was observed in the K5 protein level by the chronic ultraviolet irradiation, this difference was not remarkable as compared with changes in the K6 and K16 protein levels.

The K6 and K16 protein levels increased due to the chronic ultraviolet irradiation were shown to maintain this increase for 6 weeks even after the termination of ultraviolet irradiation and to be decreased by the CLP application. On the other hand, the K1, K10, K5, and K14 protein levels were shown to be hardly changed by the chronic ultraviolet irradiation and by the CLP application.

These results suggested that CLP allows K6 and K16 protein levels increased due to chronic ultraviolet irradiation to decrease and recover to an unirradiated or equivalent state, thereby modifying the composition of epidermal keratin proteins, leading to improvement in wrinkles.

Example 2

Test of Inhibitory Effect of CLP on Wrinkle Formation and Analysis of Epidermal Keratin Levels The same 6- to 8-week-old hairless mice as in Reference Example 1 were used and exposed to ultraviolet rays of 1 MED (minimum erythema dose) or lower. Immediately after the ultraviolet irradiation, procedures for applying 100 μL of 4% (Wt/Vol %) CLP solution (solvent: 30 Vol/Vol % ethanol/water solution) or vehicle control to the whole dorsal skin of each of the mice were performed once a day and five times a week for 12 consecutive weeks. The irradiation dose was 470 J/m² during the 0th (at the start of irradiation) to first week, 530 J/m² during the first to second week, 600 J/m² during the second to third week, and 670 J/m² during the fourth and subsequent weeks. Each of the groups comprised 10 to 12 mice.

The degree of wrinkles formed on the dorsal skins of the mice was determined after 12 weeks from the start of ultraviolet irradiation according to the visual observation score in the same way as in Reference Example 1.

Moreover, the quantification of keratin proteins was performed by western blotting in the same way as in Example 1.

Figure 6:
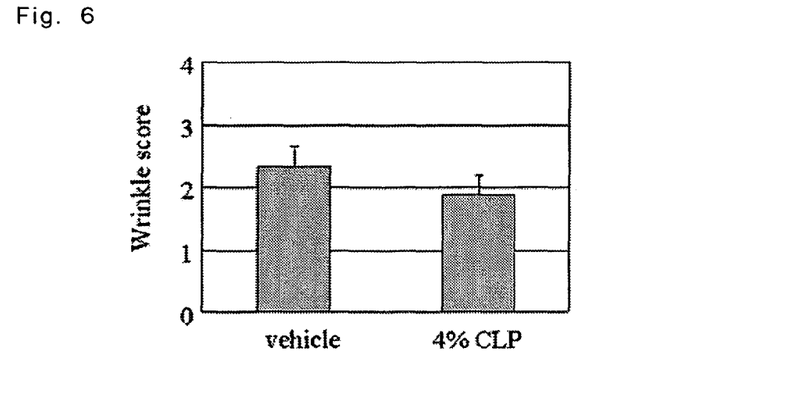
FIG. 6 is a diagram showing the inhibitory effect of CLP on wrinkle formation (evaluation of visual observation score of wrinkles)
Figure 7:
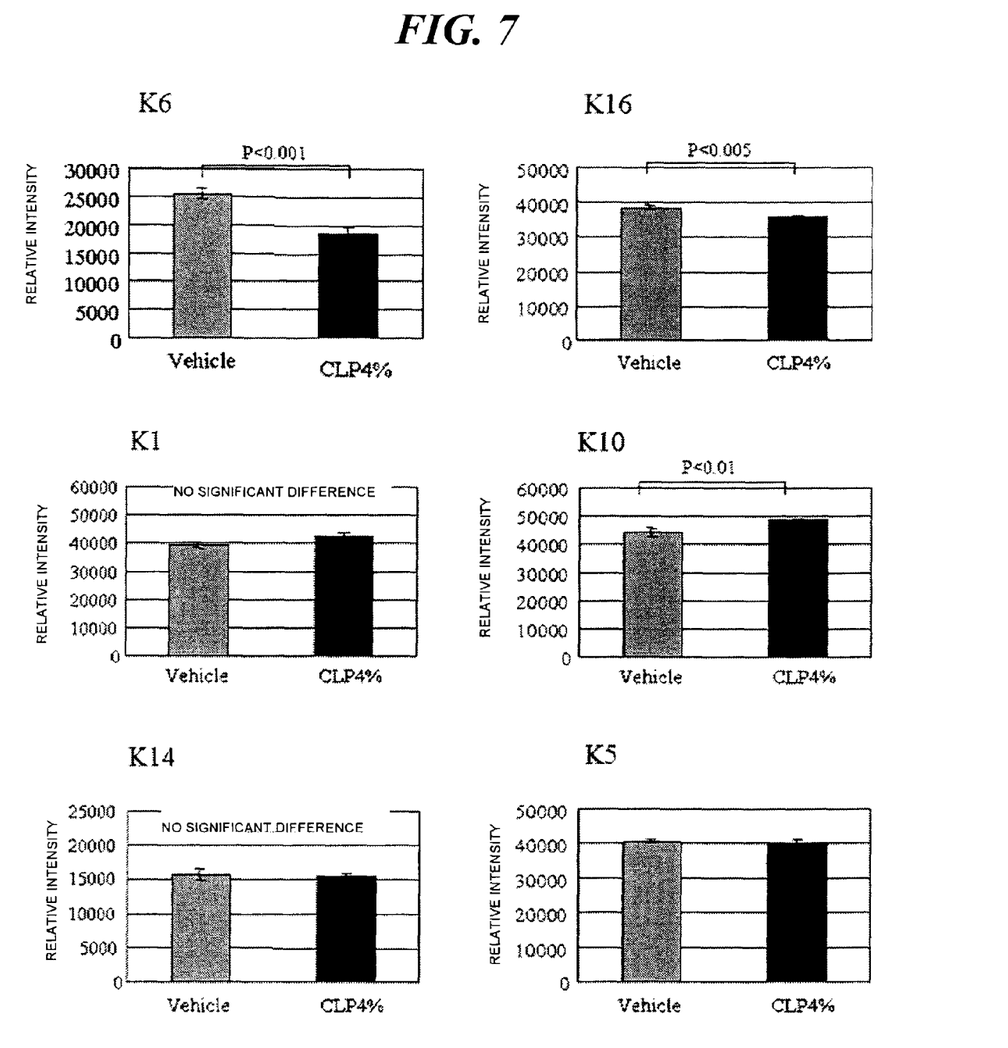
FIG. 7 is a diagram showing quantification results of K6, K16, K1, K10, K5, and K14 proteins.

As a result, a significant inhibitory effect on wrinkle formation was observed in the 4% CLP-applied group as compared with the vehicle control group (FIG. 6) Of keratin proteins in the stratum corneum of the epidermis, the K6 and K16 protein levels were significantly decreased in the CLP-applied group as compared with the vehicle control group (FIG. 7). On the other hand, no significant difference in the K1, K10, K5, and K14 protein levels was observed between the CLP-applied group and vehicle control group.

Example 3

Quantitative RT-PCR Analysis of Keratins

1. Skin Grafting

A skin graft was transplanted to each of immunodeficient mice (female, 4-6 week old). Throughout the experiment period, the mice were raised under pathogen-free conditions.

Immediately before transplantation of the skin graft, the dorsal hair was removed with an electric shaver, and isofluorane/oxygen (3%/0.8 liter) was used for anesthesia. During the grafting surgery, anesthetic conditions were maintained by use of isofluorane/oxygen (2%/0.7 liter). The dorsal skin of each mouse was scraped, to thereby produce a wound bed having a diameter of about 2.0-3.0 cm. A supplied skin graft; i.e., prepuce from circumcision, a patch of skin from plastic surgery, or a patch of skin from a cadaver supplied by the Skin Center, was grafted and sutured. The supplied patch of skin had been preserved in DMEM supplemented with L-glutamine and an antibiotic/antimycotic (Invitrogen, CA) until grafting (2-4° C.). After suturing, analgesic treatment was performed by adding sensorcaine to the boundary between the skin graft and mouse skin. Until recovery from the anesthetic, the mice were accommodated in a 37° C. incubator.

2. UV-B Irradiation

UV-B Irradiation was started after healing; i.e., at least 10 weeks after the transplantation surgery. A UV lamp which emits UV-B light having a peak in the vicinity of 302 nm wavelength was employed, and the distance between the lamp and the skin graft was about 30 cm.

Since MED (minimal erythema dose) of the transplanted skin was found to correspond to 50 to 80 $mJ/cm^2$, chronic irradiation of UV-B was decided to be started from a level of 80 $mJ/cm^2$. Irradiation was performed 5 days per week for 6 consecutive weeks. Before entering the third week, UVdose was increased by 10 $mJ/cm^2$ per week, and during the third to the sixth week, the dose of UV-B irradiation was maintained at 100 $mJ/cm^2$. During irradiation, the mice were allowed to freely move around in a transparent container having a floor area of 100 $cm^2$.

3. Quantitative RT-PCR Analysis of Keratins

Real-time quantitative reverse transcription polymerase chain reaction (RT-PCR) After chronic UVB irradiation, the transcript expression of keratins K1, K5, K6, K10, and K16 in grafted foreskin was examined using real-time quantitative RT-PCR normalized against glyceraldehyde-3-phosphate dehydrogenase (GAPDH). The grafted foreskin was immersed in RNA later (Qiagen, Valencia, Calif.) to prevent RNA degradation. Total RNA from each sample was prepared using a RNeasy microkit (Qiagen) cDNA was then synthesized by reverse transcription of total RNA using oligo dT and Moloney murine leukemia virus reverse transcriptase. On-demand probes for the genes described above in TaqMan Gene Expression Assays (Applied Biosystems, Foster City, Calif.) were used. Real-time quantitative RT-PCR with Taq-Man Gene Expression Assays was performed in an ABI PRISM 7300 sequence detection system (Applied Biosystems).

Figure 8:
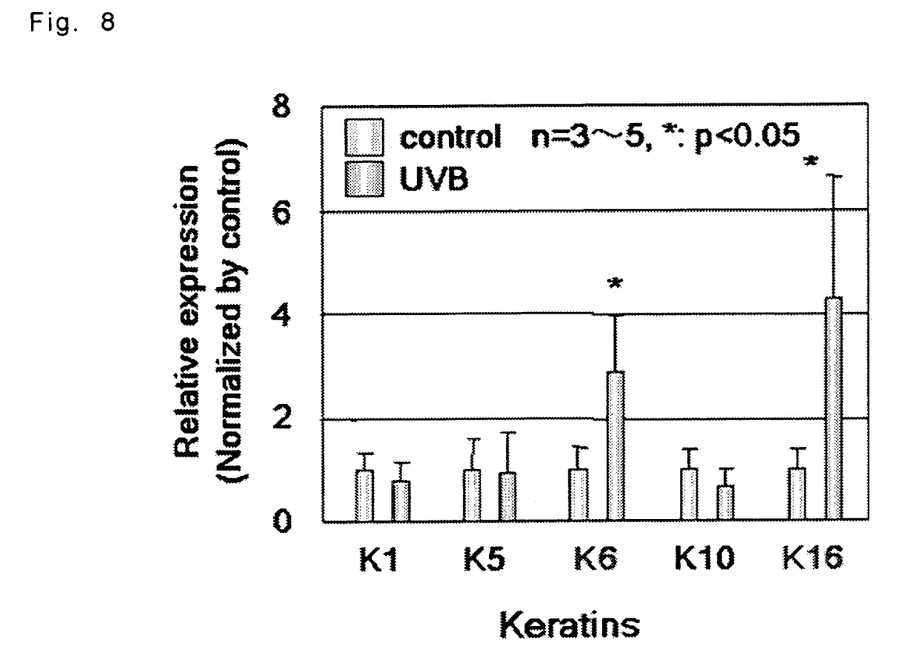
FIG. 8 is a diagram showing expression levels of K1, K5, K6, K10, and K1 genes.

As can be seen from FIG. 8, expression levels of K6 and/or K16 genes in tissues of the chronically UVB-irradiated skins of the photoaging/wrinkle formation model experimental system were remarkably increased due to ultraviolet irradiation. This indicates that the selection of a substance inhibiting the expression of keratin 6 and/or keratin 16 genes as a candidate is effective in a screening method for a photoaging- or wrinkle-preventing or improving agent.

What is claimed is:

1. A screening method for a photoaging- or wrinkle-preventing or improving agent, which selects, as a candidate, a substance inhibiting an expression of keratin 6 and/or keratin 16 genes or keratin 6 and/or keratin 16 proteins in a skin tissue or cell, wherein the skin tissue and/or cells are derived from a subject that has been exposed to UVB irradiation.

2. The screening method according to claim 1, wherein the skin tissue or cell is derived from a subject having the enhanced expression of keratin 6 and/or keratin 16 genes or keratin 6 and/or keratin 16 proteins due to an exposure to ultraviolet irradiation of 1 minimum erythema dose (MED) or lower for 4-20 consecutive weeks.

3. A screening method for a photoaging- or wrinkle-preventing or improving agent, comprising:
   (1) bringing a test substance into contact with a skin tissue or cell having the enhanced expression of keratin 6 and/or keratin 16 proteins;
   (2) extracting epidermal keratin proteins from the skin tissue or cell;
   (3) measuring expression levels of keratin 6 and/or keratin 16 proteins in the extracted epidermal keratin proteins and comparing the expression levels with expression levels of keratin 6 and/or keratin 16 proteins in a control skin tissue or cell not brought into contact with the test substance; and
   (4) selecting the test substance decreasing the expression levels of keratin 6 and/or keratin 16 proteins as a photoaging- or wrinkle-preventing or improving agent, based on the result of the step (3),
   wherein the skin tissue or cell are derived from a subject that has been exposed to ultraviolet radiation of 1 minimum erythema dose (MED) or lower for 4-20 consecutive weeks before (1).

4. A screening method for a photoaging- or wrinkle-preventing or improving agent, comprising:
   (1) bringing a test substance into contact with a skin tissue or cell having the enhanced expression of keratin 6 and/or keratin 16 genes;
   (2) measuring expression levels of keratin 6 and/or keratin 16 genes in the tissue or cell brought into contact with the test substance and comparing the expression levels with expression levels of keratin 6 and/or keratin 16 genes in a control skin tissue or cell not brought into contact with the test substance; and
   (3) selecting the test substance decreasing the expression levels of keratin 6 and/or keratin 16 genes as a photoaging- or wrinkle-preventing or improving agent, based on the result of the step (2),
   wherein the skin tissue or cell are derived from a subject that has been exposed to ultraviolet radiation of 1 minimum erythema dose (MED) or lower for 4-20 consecutive weeks before (1).

5. The screening method of claim 3, further comprising measuring expression levels of keratin 1 and keratin 14 in the skin tissue or cell, wherein the expression levels of keratin 1 and keratin 14 do not change statistically significantly in the skin tissue or cell irradiated with UVB compared to the expression levels of keratin 1 and keratin 14 in a skin tissue or cell not irradiated with UVB.

6. The screening method of claim 4, further comprising measuring expression levels of keratin 1 and keratin 14 genes in the skin tissue or cell, wherein the expression levels of keratin 1 and keratin 14 genes do not change statistically significantly in the skin tissue or cell irradiated with UVB compared to the expression levels of keratin 1 and keratin 14 genes in a skin tissue or cell not irradiated with UVB.

7. The screening method of claim 2, further comprising measuring expression levels of keratin 1, keratin 10, keratin 5, and keratin 14 genes in the skin tissue or cell, wherein keratin 1, keratin 10, keratin 5, and keratin 14 do not change statistically significantly the expression levels in the skin tissue or cell irradiated with UVB compared to the expression levels of keratin 1, keratin 10, keratin 5, and keratin 14 genes in a skin tissue or cell not irradiated with UVB.

8. The screening method of claim 3, wherein the expression level of keratin 6 and/or keratin 16 protein in the UVB irradiated skin tissue or cell is increased by about 120 to 300% for keratin 6 and about 120 to 200% for keratine 16 compared to a normal skin tissue or cell.

9. The screening method of claim 4, wherein the expression level of keratin 6 and/or keratin 16 genes in the UVB irradiated skin tissue or cell is increased by about 120 to 500% compared to a normal skin tissue or cell.

10. The screening method of claim 5, wherein the expression level of keratin 6 and/or keratin 16 protein in the UVB irradiated skin tissue or cell is increased by about 120 to 300% for keratin 6 and about 120 to 200% for keratine 16 compared to a normal skin tissue or cell.

11. The screening method of claim 6, wherein the expression level of keratin 6 and/or keratin 16 genes in the UVB irradiated skin tissue or cell is increased by about 120 to 500% compared to a normal skin tissue or cell.

12. The screening method of claim 1, wherein the skin tissue or cells are derived from an epidermal portion of the skin of the subject comprising stratum corneum.

13. The screening method of claim 2, wherein the skin tissue or cells are derived from an epidermal portion of the skin of the subject comprising stratum corneum.

14. The screening method of claim 3, wherein the skin tissue or cells are derived from an epidermal portion of the skin of the subject comprising stratum corneum.

15. The screening method of claim 4, wherein the skin tissue or cells are derived from an epidermal portion of the skin of the subject comprising stratum corneum.

16. The screening method of claim 5, wherein the subject is an immunodeficient mouse comprising a human skin graft, and the skin tissue and/or cells are derived from the graft.

17. The screening method of claim 6, wherein the subject is an immunodeficient mouse comprising a human skin graft, and the skin tissue and/or cells are derived from the graft.

18. The screening method of claim 7, wherein the subject is an immunodeficient mouse comprising a human skin graft, and the skin tissue and/or cells are derived from the graft.

* * * * *